(12) United States Patent
Atashbar et al.

(10) Patent No.: US 8,510,056 B2
(45) Date of Patent: Aug. 13, 2013

(54) METHOD AND INTEGRATED MICROSYSTEM FOR DETECTING BIOMOLECULES IN LIQUID

(75) Inventors: Massood Zandi Atashbar, Kalamazoo, MI (US); Bruce Evan Bejcek, Portage, MI (US)

(73) Assignee: Western Michigan University Research Foundation, Kalamazoo, MI (US)

( * ) Notice: Subject to any disclaimer, the term of this patent is extended or adjusted under 35 U.S.C. 154(b) by 514 days.

(21) Appl. No.: 12/084,085

(22) PCT Filed: Oct. 23, 2006

(86) PCT No.: PCT/US2006/041408
§ 371 (c)(1),
(2), (4) Date: Jul. 26, 2010

(87) PCT Pub. No.: WO2008/136787
PCT Pub. Date: Nov. 13, 2008

(65) Prior Publication Data
US 2010/0291711 A1    Nov. 18, 2010

Related U.S. Application Data

(60) Provisional application No. 60/729,568, filed on Oct. 24, 2005.

(51) Int. Cl.
*G01N 33/48* (2006.01)
(52) U.S. Cl.
USPC .......................................................... 702/19

(58) Field of Classification Search
None
See application file for complete search history.

(56) References Cited

FOREIGN PATENT DOCUMENTS
WO    WO/03/046536    *    6/2003

OTHER PUBLICATIONS

Caruso et al. (Anal. Chem. 1997, 69, 2043-2049).*
Nguyen et al. (Sensors and Actuators, 1999, 77, 229-236).*
Fredriksson et al. (Journal of Materials Science: Materials in Medicine, 1998, 9, 785-788).*
Sia et al., "Microfluidic devices fabricated in poly(dimethylsiloxane) for biological studies", Electrophoresis 2003, 24, 3563-3576, 2003 WILEY-VCH Verlag GmbH & Co. KGaA, Weinheim.
Hongkai Wu et al., "Fabrication of Complex Three-Dimensional Microchannel Systems in PDMS", J.Am.Chem. Soc. 2003, 125, 554-559, 2003 American Chemical Society.

* cited by examiner

*Primary Examiner* — Pablo S Whaley
(74) *Attorney, Agent, or Firm* — Price Heneveld LLP

(57) ABSTRACT

The present invention is directed to an integrated microsystem and method for detecting biomolecules in a liquid sample. The integrated microsystem is made up of a sensor that includes microelectrodes connected to a matrix of carbon nanotubes deposited on a substrate, a micropump, a microcontroller for regulating the sample delivery, a signal processor for analyzing the sensor signal, a microheater that surrounds the carbon nanotube sensor, and microfluidic channel formed by a polydimethylsiloxane (PDMS) silicone elastomer cap containing a trench with the cap aligned with the carbon nanotube sensor. The method includes using the integrated microsystem to detect the presence of a biomolecule based on changes in the electrical conductance or resonant frequency of the carbon nanotube matrix.

11 Claims, 6 Drawing Sheets

■ Aluminum ■ Photoresist □ Silicon ■ Silicon Dioxide ▨ Zinc Oxide

METHOD AND INTEGRATED MICROSYSTEM FOR DETECTING BIOMOLECULES IN LIQUID

CROSS-REFERENCE TO RELATED APPLICATION

This application is the National Stage of International Application No. PCT/US2006/041408, filed Oct. 23, 2006, which claims the benefit of U.S. Provisional Application No. 60/729,568, filed Oct. 24, 2005, which is hereby incorporated by reference herein in its entirety.

FIELD OF THE INVENTION

The present invention is directed to an integrated microsystem which can be used in the detection of biomolecules. In particular, the present invention is directed to an integrated microsystem which utilizes sensors to detect the presence of a target biomolecule.

BACKGROUND OF THE INVENTION

Single Wall Carbon nanotubes (SWNTs) can be realized as graphite sheets that have been rolled into seamless cylinders. Ever since Carbon nanotubes (CNTs) discovery by Iijima in 1991, they have been treated as the most promising nanostructured materials. S. Iijima, "Helical microtubules of graphitic carbon", Nature, vol. 354, pp. 56-58, November 1991. Carbon nanotubes exhibit both semiconducting and metallic behavior depending on their chirality. J. W. G. Wildoer, L. C. Venema, A. G. Rinzler, R. E. Smalley, and C. Dekker, "Electronically structure of atomically resolved carbon nanotubes", Nature, vol. 391, pp. 59-61, January 1998. This special property of nanotubes makes them the ideal choice for interconnects and also as active devices of nanoelectronics. CNTs have been used as chemical sensors for the detection of hazardous gasses such as $NH_3$ and $NO_2$. J. Kong, N. R. Franklin, C. Zhou, M. G. Chapline, S. Peng, K. Cho, and H. Dai, "Nanotube molecular wires as chemical sensors", Science, vol. 287, pp. 622-625, January 2000. The application of these quantum wires as biological sensors is a new facet which might find significant applications in the life sciences field and it has been recently demonstrated that individual semiconducting single wall carbon nanotubes can be used for the detection of glucose oxidase. R. J. Chen, H. C. Choi, S. Bangsaruntip, E. Yenilmez, X. Tang, Q. Wang, Y. Chang, and H. Dai, "An investigation of the mechanisms of electronic sensing of protein adsorption on carbon nanotube devices", Journal of American Chemical Society, vol. 126, pp. 1563-1568, January 2004. K. Besteman, J. Lee, F. G. M. Wiertz, H. A. Heering, and C. Dekker, "Enzyme-coated carbon nanotubes as single-molecule biosensors" Nanoletters, vol. 3, pp. 727-730, April 2003.

Recently acoustic wave sensors have been used for many applications in detecting chemical components in liquid media. By using the so-called chemical interfaces, they can be implemented for determining the concentration of a highly specific target compound in a liquid environment. The chemical interface selectively adsorbs materials in the solvent to the surface of the sensing area. Due to the change in the mass, the perturbation in the physical and chemical properties of the surface changes the phase and amplitude of the acoustic and electromagnetic fields on the surface. These changes can be monitored as the related change of mass.

Acoustic wave based sensors include those based on devices such as the Thickness Shear Mode (TSM), Surface Acoustic Wave (SAW), the Shear Horizontal Surface Acoustic Wave (SH-SAW), the Shear Horizontal Acoustic Plate Mode (SH-APM), and the Flexural Plate Wave (FPW). In a liquid environment, longitudinal bulk modes and Rayleigh waves cannot be used due to strong radiation losses into the liquid. Therefore, acoustic shear wave modes, which do not couple elastically to the liquid, are utilized; hence devices such as TSM, SH-SAW, Love modes, SH-APM and FPW are proper candidates for the development of devices to detect biomolecules in complex mixtures such as those represented by serum samples.

Since acoustic wave devices use piezoelectric materials for the excitation and the detection of acoustic waves, the nature of almost all of the parameters involved with sensor applications concerns either mechanical or electrical perturbations. An acoustic device is thus sensitive mainly to physical parameters, which may interact (perturb) with mechanical properties of the wave and/or its associated electrical field. For biological sensors, the binding of the antibodies and antigens on the substrate changes the mass of the membrane thus causing a drop in the wave velocity, which is correlated to the resonance frequency of the device.

Recent research in chemical sensing and microbiology has increased the quest for practical and inexpensive microfluidic devices. Different approaches for delivering samples through the microfluidic devices using micropumps have been investigated. However, most micropumps are not suitable for transporting fluid for this proposed microsystem due to performance dependency on temperature (thermal bubble pump and electrohydrodynamic pump), or concentration of ions in the sample (electroosmotic pump). Further, micropumps using valves or diffuser elements (electrostatically actuated pump and diffuser pump) are also not suitable as they present high impedance in the channel.

An acoustic micropump, such as the FPW micropump, has recently become known. The operating principle of this pump is based on the phenomenon of acoustic streaming, in which the fluid flows in the direction of the acoustic wave, eliminating valves, diffuser and dependency on temperature and ion concentrations. N. T. Nguyen, R. W. Doering, A. Lal, R. M. White, "Computational fluid dynamics modeling of flexural plate wave pumps", Proceedings" IEEE Ultrasonics Symposium, Vol. 1, (1998) 431. N. T. Nguyen, X. Huang, T. K. Chuan, "MEMs-micropumps: a review", Transactions of the ASME. Journal of Fluids Engineering, Vol. 124, No. 2, (2002) 384. N. T. Nguyen, A. H. Meng, J. Blac, and R. M. White, "Integrated flow sensor for in situ measurement and control of acoustic streaming in flexural plate wave micropumps, Sensors and Actuators A: Physical, Vol. 79, No. 2, (2000) 115.

Bradley et al have demonstrated the use of FPW micropump to produce a unidirectional flow with a velocity of about 150 μm/s. C. E. Bradley, J. M. Bustillo, R. M. White, "Flow measurements in a micromachined flow system with integrated acoustic pumping", Proceedings: IEEE Ultrasonics Symposium, Vol. 1, (1995) 505. A conventional FPW transducer launches waves that add constructively in both the forward and the backward directions, thus giving bi-directional waves.

SUMMARY OF THE INVENTION

The present inventors have fabricated a simple yet efficient carbon nanotube conductance based sensor for the detection of biomolecules. In addition, Quartz Crystal Microbalance (QCM) was used to quantify the mass of the biomolecules bound on the surface of the nanotubes. The sensors are used in an integrated microsystem comprising a micropump, a microheater, a microcontroller and a signal processor to identify the presence of a target molecule in a liquid sample.

The single wall carbon nanotube (SWNT) based biological sensor for the detection of biomolecules usable in the present invention employs two types of sensing mechanisms. Firstly, the changes in the electrical conductance of the carbon nanotube matrix on noncovalent binding of the biomolecules to the side walls of the carbon nanotube and secondly, quantification of mass uptake of the matrix on biomolecule incubation are presented. Both sensing mechanisms exhibited consistent and highly sensitive responses.

DETAILED DESCRIPTION

Streptavidin from *Streptomyces avidinii* was purchased as a lyophilized powder from the Sigma-Aldrich Company. The Protein was dissolved in phosphate buffered saline (PBS, Sigma-Aldrich) and stored as aliquots at $-20°$ C. Mouse monoclonal IgG was purchased from Bio Design International Inc. The antibody solution was resuspended in PBS and stored frozen at $-20°$ C. until use.

Single wall Carbon nanotubes (70% pure with nickel and yttrium as catalyst residue) were purchased from Corbolex Inc. The SWNTs were dissolved in chloroform and then filtered through 0.02 µm pore size Anatop filters (Whatman). The filtered solution was then sonicated to derope the bundled CNTs. The CNTs 2 were then casted on a glass substrate 3 using a micropipette. The glass substrate 3 was cleaned before casting SWNT solution with isopropyl alcohol to remove any contamination on the surface. The thickness of the film was controlled by the amount of casted solution and its concentration. The matrix of the SWNT 2 was studied using Atomic Force Microscope (Thermomicroscopes Auto Probe CP Research machine) in non-contact mode. The thickness was measured using AFM by scanning along the edge of an artificially made scratch on the film.

Figure 1:
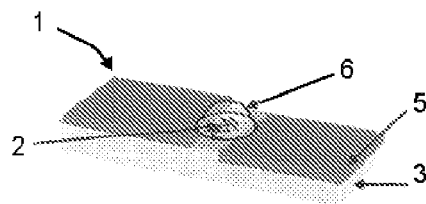
FIG. 1 is a schematic representation of a sensor according to the present invention.

Microelectrode contacts 5 across the matrix were formed by thermal evaporation of silver. The shadow masking technique was employed to form the gap between the electrodes. A tungsten wire (Sylvania) with a diameter of 60 µm was wrapped around the glass substrate to mask the area of the CNT. After silver evaporation, the tungsten wire was removed leaving the CNTs with the electrodes across them to form the sensor 1, as shown in FIG. 1. Agilent multimeter (Agilent-3458A) was employed to monitor the electrical changes of the CNT matrix which was interfaced with a computer. A constant voltage was applied between the electrodes and the conductance changes for various concentrations of the protein and antibody were recorded. Protein solutions were added to 10 µl of PBS that had been placed on the sensor. PBS 6 was employed as a buffer environment to distinguish changes in CNT matrix conductivity due to protein binding.

Quartz Crystal Microbalance (Stanford Research Systems QCM100) with 5 MHz AT-cut quartz crystals (gold coated) was used to quantitatively study the ability of the CNTs to bind streptavidin and mouse monoclonal IgG. CNT solution was casted on the gold surface and then the crystal was baked at $50°$ C. for two hours. The CNT presence on the surface of the crystal was verified by Raman spectroscopy. The Raman spectrometer (Detection Limit Inc) was equipped with a laser source of 633 nm wavelength and energy of 1.96 eV.

Fabrication and Packaging of the FPW Sensor

Figure 18:
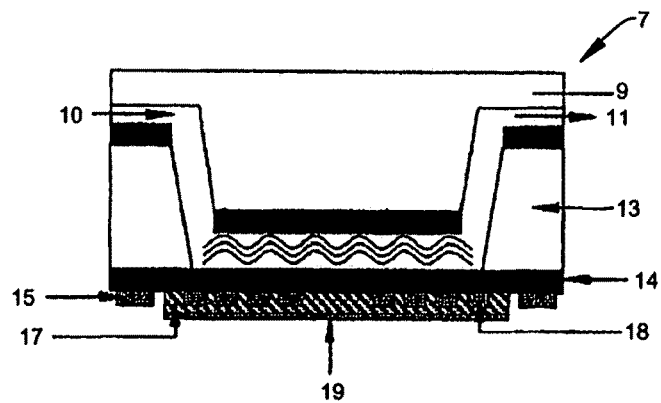
FIG. 18 illustrates the cross-section of the sensor and its flow cell.
Figure 19A:
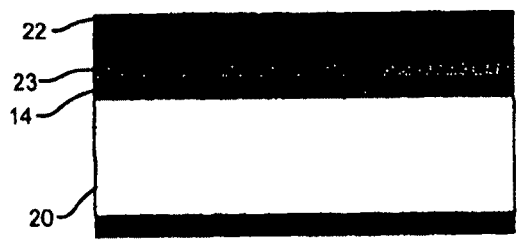
FIGS. 19(a)-(f) show the fabrication steps of the sensor of the present invention.
Figure 19B:
Figure 19C:
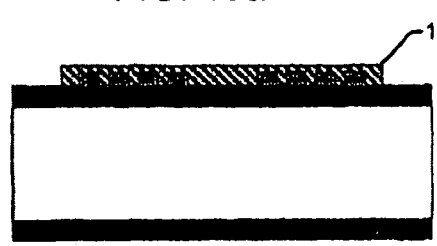
Figure 19D:
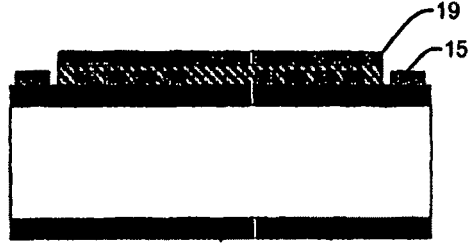
Figure 19E:
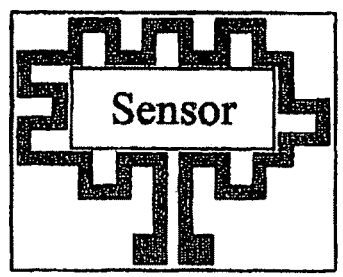
Figure 19F:
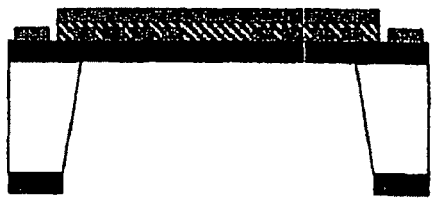

FIG. 18 shows the cross-section of the sensor and its liquid cell 7. The FPW chip and liquid cell will be fabricated separately and subsequently attached and sealed together using silicone rubber as a molding 9.

The sensor-flow cell 7 is made up of a liquid passage inlet 10, liquid passage outlet 11, sensor chip B, silicon dioxide layer 14, heater 15, zinc oxide layer 17, interdigitated transducers and ground plane 19. The requirements for the liquid cell design include: minimization of the overall cell dimensions; use of a suitable inert material and minimization of the applied pressure for maintaining the liquid seal. Furthermore, for biosensing investigations sample liquid volumes are usually restricted to the microliter range, where larger volumes are generally not desirable due to cost and availability. Small liquid cell volumes also have the benefit of facilitating rapid sample and reference liquid changes, contributing to a reduction in the delay and response times of the sensor. A liquid cell was fabricated using a silicon substrate with an internal liquid volume of about 12 µl.

FIGS. 19(a)-(f) show the cross-sections of the fabrication steps. The FPW system was fabricated in a clean room environment. The fabrication steps are as follows:

1. Cleaning of the silicon wafer in a combination of chemical baths to remove any impurities from the wafer surface.

This will be achieved by treating the wafer in Piranha solution (one part 30% $H_2O_2$ and three parts concentrated $H_2SO_4$) followed by a thorough rinsing with distilled/deionized water.

2. Incubation in a high temperature furnace (approximately for 15 minutes at 900° C. in a $H_2O$ atmosphere) to thermally grow a layer of silicon dioxide ($SiO_2$) on both sides of the wafer.

3. Aluminum layer 23 will be deposited on the $SiO_2$ layer 14, followed by spin coating a photoresist layer 22 onto the wafer with a thickness of 1 μm, as shown in FIG. 19(*a*).

4. Baking of the wafer at 100° C. to evaporate any residual solvents. Subsequently, the photoresist was exposed using a mask, which defines the pattern for the aluminum interdigitated transducers (IDTs) 18. This is shown in FIG. 19(*b*). Two sets of IDTs 18 were patterned. The remaining photoresist was then removed by standard photolithographic techniques.

5. A Zinc Oxide (ZnO) layer 17 was RF-sputtered onto the wafer. This was patterned using a second mask photolithography process as illustrated in FIG. 19(*c*).

6. Sputtering of an aluminum layer onto the wafer to form the ground plane 19 and the microheater 15 using third mask photolithography process that is shown in FIG. 19(*d*) (cross section) and FIG. 19(*e*) (top) views respectively.

A deep boron diffusion step was performed to release the membrane and to define the etch stop limit. Then the silicon chip was back-etched as shown in FIG. 19(*f*). To do this the photoresist was spun and the region for the window defined using the fourth mask photolithography process.

Fabrication steps for creating the FPW micropump 25 was exactly the same as those for the fabrication of the FPW sensor 26. However, the orientation and spacing of the IDTs was optimized to insure that this FPW will act as a pump. Initially IDTs will be spaced a quarter of wavelength apart to generate unidirectional acoustic waves as previously reported. C. E. Bradley, J. M. Bustillo, R. M. White, "Flow measurements in a micromachined flow system with integrated acoustic pumping", Proceedings: IEEE Ultrasonics Symposium, Vol. 1, (1995) 505. The micropump and sensor 26 will therefore be fabricated on a chip to create the total micropump/sensor as a single unit 27. The ideal temperature for operation will be maintained by a microheater surrounding the sensor. This will be achieved using platinum microheater fabricated on silicon substrate by standard techniques. G. S. Chung and S. S. Noh, "Fabrication of the Pt microheater using aluminum oxide as a medium layer and its characteristics", Sensors and Actuators, Vol. 10, No. 5, (1998) 251.

Figure 20:
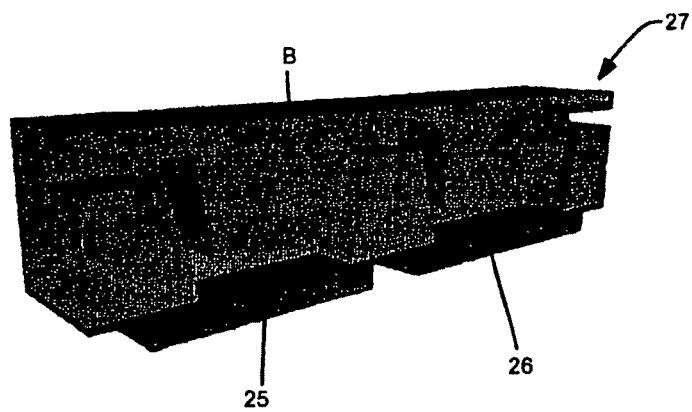
FIG. 20 is a cross-section of the integrated sensor/pump chip flow channel.

To create a fluid microchannel, a cap was fabricated by forming trenches in polydimethylsiloxane (PDMS) silicone elastomer using soft lithography technique with the same considerations as C. E. Bradley, J. M. Bustillo, R. M. White, "Flow measurements in a micromachined flow system with integrated acoustic pumping", Proceedings: IEEE Ultrasonics Symposium, Vol. 1, (1995) 505. Then the cap was aligned with the sensor/pump chip. Hence a microchannel was created for the fluid flow. FIG. 20 illustrates the cross section of the integrated sensor/pump chip flow channel.

EXAMPLE 1

Purification of CNT

Figure 2:
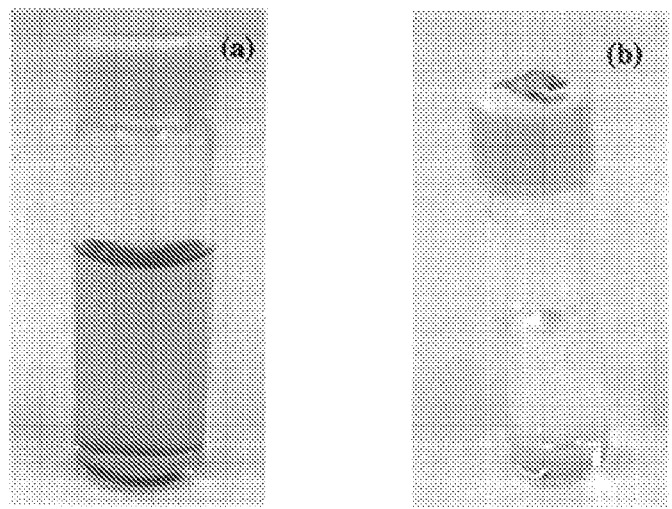
FIG. 2A illustrates a solution of carbon nanotubes before filtration and FIG. 2B illustrates the solution after filtration.

The CNTs were dissolved in chloroform (Sigma-Aldrich) and then casted on silicon substrates. However AFM imaging of the samples revealed that there was a high content of catalyst residue. Filtration of the CNT solution using antop filters resulted in transparent solution. FIG. 2 shows the photograph of the CNT solution before and after filtration. It is known that the carbon nanotubes have a tendency to form into parallel bundles resulting to triangular lattice because of the inter-molecular van der Waals forces between the nanotubes. To overcome the inter-molecular forces, the filtered CNT solution was sonicated for one hour.

Figure 3:
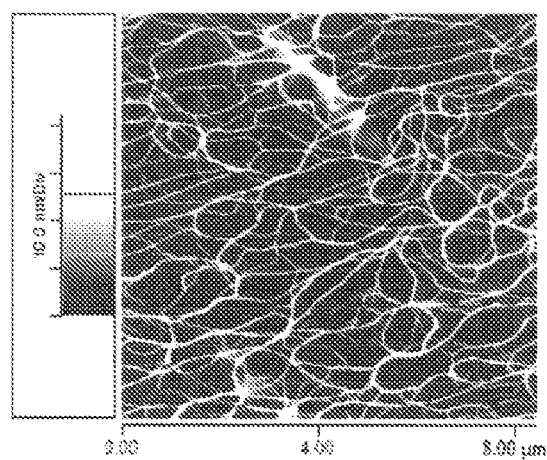
FIG. 3 is a micrograph of a carbon nanotube matrix deposited on a substrate.

FIG. 3 shows uniformly distributed casted CNT matrix on the silicon substrate. It can be observed that most of the undesired catalyst residue has been filtered out leaving behind the nanotubes.

Figure 4:
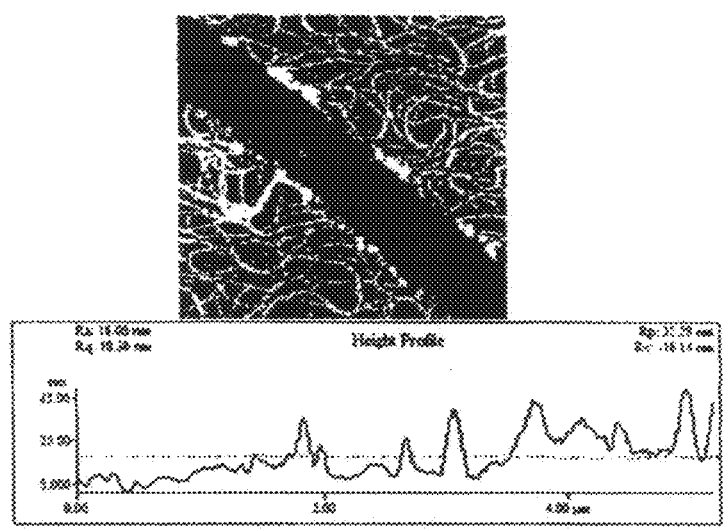
FIG. 4 is a micrograph of a carbon nanotube matrix illustrating its scratch and height profile.

The thickness of the CNT film was controlled by the amount of solution casted and the concentration of the solution. FIG. 4 shows the micrograph of the CNT film and its height profile showing that the film thickness was approximately 20 nm.

Electrical Characterization

Figure 5:
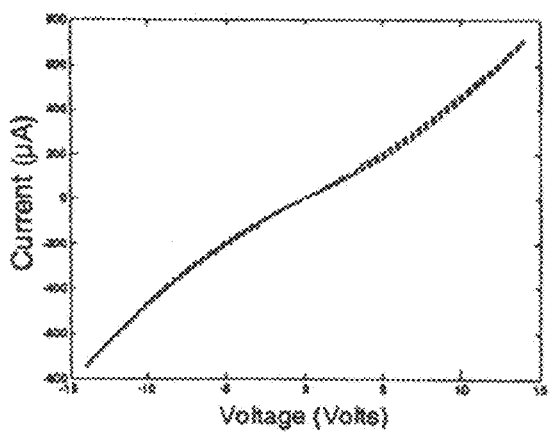
FIG. 5 is a graph showing the electrical characteristics of the carbon nanotube matrix.

Electrical characteristics of the sensor were studied using microelectrodes patterned by shadow masking technique as described above. FIG. 5 shows the electrical characteristics of the CNT matrix. The matrix demonstrated semiconducting behavior. This behavior is in agreement with the fact that a randomly selected CNT sample contains approximately 70% semiconducting nanotubes while the rest are metallic. This makes the entire matrix to be semiconducting in nature.

Sensor Responses

Figure 6:
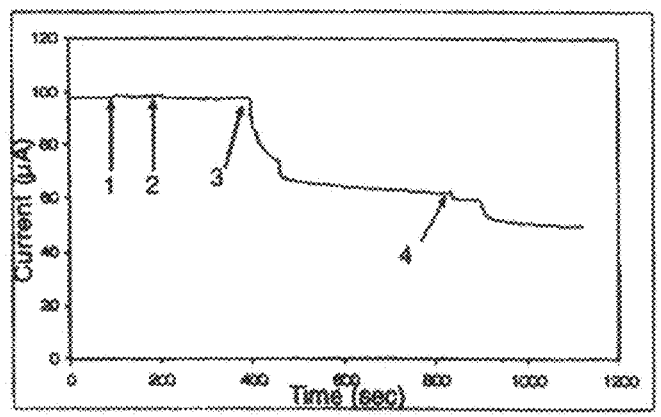
FIG. 6 illustrates the electrical responses of a sensor of the present invention with respect to various concentrations of streptavidin.

Five microliters of a solution of Streptavidin with different concentrations was added to the 10 μl of PBS to result in 10 nM, 1 μM and 2 μM of protein. FIG. 6 shows the electrical response of the sensor to different protein concentrations. Point 1 indicates the instance at which 10 μl of PBS was introduced between the electrodes and point 2 is the time at which 5 μl streptavidin solution was added to the PBS making the final concentration of the protein to be 10 nM. It can be seen that there was no appreciable change in the current. The protein concentration was increased to 1 μM at Point 3 and a decrease in the conductance of the CNT matrix was observed. The current decreased from 97.7 μA to 60.3 μA which corresponds to approximately a 40% change in conductance. After the current stabilized, the protein concentration was further increased to 2 μM and a further decrease in current was recorded. The change in conductance was 17.5% (60.3 μA to 49.7 μA) which is smaller compared to the initial change.

The smaller change in the conductance can be attributed to less number of active sites available for the protein molecules to bind to CNT.

Figure 7:
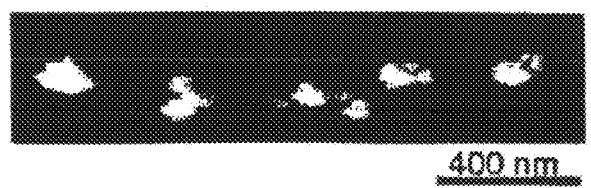
FIG. 7 is an AFM micrograph showing protein molecules bound on the sidewalls of a carbon nanotube.

FIG. 7 is an AFM micrograph of the CNT and protein molecules. From this Figure it can be seen that protein molecules were bound on the sidewalls of the tube and bundles of CNT were decorated with streptavidin molecules.

Figure 8:
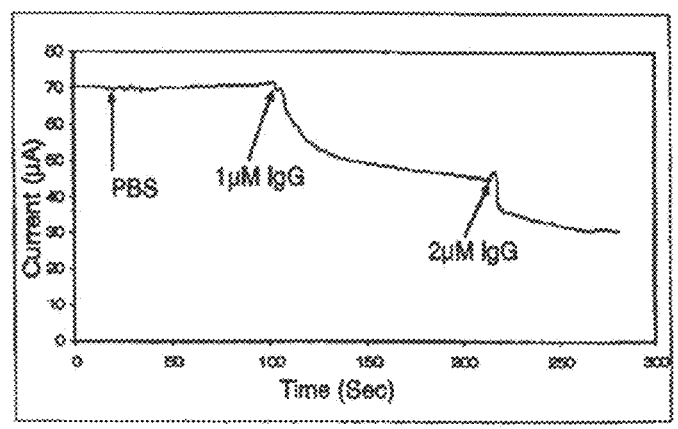
FIG. 8 is a graph illustrating the electrical responses of a sensor of the present invention with respect to various concentrations of IgG.

FIG. 8 shows the sensor response to the mouse monoclonal IgG. Following introduction of PBS and 1 μM of IgG the current decreased from 71.2 μA to 45.4 μA which is nearly a 36% change in conductance. With increase of concentration to 2 μM, the current further decreased to 30 μA which is a 30% change. This is consistent with Streptavidin behavior which can be attributed to less number of active sites available for binding of IgG to CNT.

The concentration of the biomolecule forms the "control" for the fine modulation of current between the electrodes. The change in the conductance can be explained in a simple way. It is known from previous studies that streptavidin is electrically neutral at a pH between 6 and 7.2. However, the surface of the protein molecule still consists of strong residual bases. These bases are responsible for charge transfer.

Figure 9:
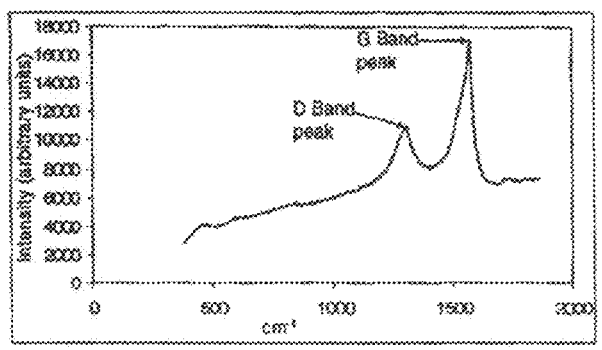
FIG. 9 is a graph showing the Raman spectrum of carbon nanotubes on a gold surface of a quartz crystal.

The quantitative study of mass uptake of CNT network due to biomolecules immobilization was performed using QCM. In QCM, a chemical interface on the surface of the sensor selectively adsorbs materials in the solvent to the surface of the sensing area. In our context, the chemical interface is the CNT matrix on the gold surface coated on the QCM crystal. The CNT matrix on the gold surface was characterized by Raman spectroscopy. A. G. S. Filho, A. Jorio, G. G. Samsonidze, G. Dresselhaus, R. Satio, and M. S. Dresselhaus, "Raman spectroscopy for probing chemically/physically induced phenomena in carbon nanotubes", Nanotechnology, vol. 14, pp. 1130-1139, September 2003. FIG. 9 shows the Raman spectrum obtained from the CNT film on the gold surface of the quartz crystal. It can be seen that the Raman spectrum has characteristic 'G' band and 'D' band peaks which arise due to the in-plane Raman-active and disorder of the CNT respectively. A. G. S. Filho, A. Jorio, G. G. Samsonidze, G. Dresselhaus, R. Satio, and M. S. Dresselhaus, "Raman spectroscopy for probing chemically/physically induced phenomena in carbon nanotubes", Nanotechnology, vol. 14, pp. 1130-1139, September 2003.

Figure 10:
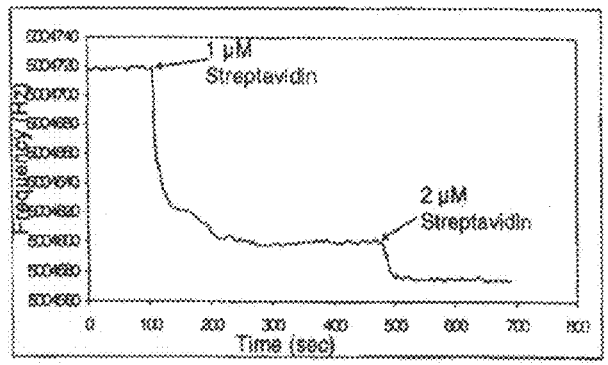
FIG. 10 is a graph showing the quartz crystal microbalance frequency response for streptavidin.

Measurements of CNT coated QCM crystals were performed by covering the chips with PBS before addition of the protein solutions. FIG. 10 depicts the QCM response using streptavidin. For a concentration of 1 µM of streptavidin a change of 120 Hz in resonant frequency was recorded. From the Sauerbrey equation the mass bound was calculated to be 1.538 µg. When the concentration on the chip was increased to 2 µM, the change in the frequency was found to be 26 Hz. This corresponds to a mass uptake of 0.33 µg. The lower frequency shift can be attributed to fewer active sites available for the protein molecules as described in the conductance based sensors. Similar results were observed for IgG with the frequency change being 248 Hz using a 2 µM concentration.

EXAMPLE 2

Materials

Protein A (Sigma-Aldrich) and mouse monoclonal IgG antibody (BioDesign International Inc) have been and will continue to be used throughout these studies. Protein A and monoclonal IgG were resuspended in phosphate buffered saline (PBS; Sigma-Aldrich) at desired concentrations and stored at −20° C. in 50 µl aliquots before use. Polystyrene, 3-Aminopropyl triethoxysilane (3-APTES), glutaraldehyde, acetone, glycine and sodium chloride were purchased from Sigma-Aldrich Chemical Company. Polystyrene dissolved in chloroform (7% w/v) was used to coat the QCM chips. Solutions of 5% 3-APTES in acetone, 5% glutaraldehyde in milli-Q water, PBS buffer with pH 7.0 in milli-Q water were prepared. 0.1M Glycine solution in milli-Q water, 0.1M glycine-HCl buffer with pH 2.4 and 0.5M NaCl solution was prepared. CNTs were purchased from Carbolex Inc.

Experimental Procedures

For promoting the immobilization of Protein A and to provide the necessary amine groups on the gold surface, the protocol of Muramatsu et al was followed. H. Muramatsu, J. M. Dicks, E. Tamiya, I. Karube, "Piezoelectric crystal biosensor modified with protein A for determination of immunoglobulins", Analytical Chemistry 59 (1987) 2760-2763. To remove any organic contamination from the surface of the crystal and improve the hydrophilic nature of the chip, it was cleaned with Piranha solution (3 parts of $H_2SO_4$ in 1 part of 30% $H_2O_2$). Enough Piranha solution was employed to cover the gold surface of the chip and allowed to incubate at room temperature for two minutes before rinsing with milli-Q water. This procedure was repeated twice. Subsequently, the chip was blow dried in a stream of nitrogen gas. A 5% solution of 3-APTES in acetone was added to create a self-assembled monolayer (SAM). After one hour, the sample was rinsed with milli-Q water after the APTES treatment to remove the physiosorbed molecules. The chip was placed in a 5% glutaldehyde solution for three hours to allow for the cross linking between the chip and the Protein A. The crystal was then covered with 20 µl solution of Protein A (0.5 mg/ml). After one hour, the solution was removed and the crystal was subjected to several wash-dry cycles with milli-Q water until the QCM crystal reached its steady resonant frequency. The chip was then covered with 0.1 M glycine dissolved in PBS for one hour to block any sites not bound to Protein A on the glutaraldehyde modified chip. The chip was then rinsed with 0.1M glycine-HCl buffer (pH 2.4) to wash off any excess proteins or glycine before being thoroughly rinsed with milli-Q water. 20 µl of the mouse monoclonal IgG solution was then incubated on the chip for one hour followed by rinsing with 0.5M NaCl to remove any non-specifically adsorbed antibody. For the experiments in which binding was measured with the polymer film, polystyrene was spin coated onto the chip at a speed of 1000 rpm and then treated with 50% (v/v) $HNO_3$ in concentrated $H_2SO_4$ for one hour. J. Kaur, K V. Singh, M. Raje, G>C> Varshney, C. R. Suri, "Strategies for direct attachment of hapten to a polystyrene support for applications in enzyme-linked immunosorbent assay (ELISA)", Analytica Chimica Acta 506 (2004) 133-135. The substrate was then modified with 3-APTES followed by glutaraldehyde as described above.

Characterization Tools and Methods

A Quartz Crystal Microbalance (Stanford Research Systems QCM 100) with 5 MHz AT-cut quartz crystals (gold coated) was used to quantitatively study the ability to bind Protein A and mouse monoclonal IgG to the chip. The gold surface, which forms the active area for immobilization was 1.37 $cm^2$ and the mass sensitivity of the crystal was 0.057 Hz/ng/$cm^2$. Frequency was monitored using a Stanford Research System Universal Time Interval Counter (Model No. SR620).

Qualitative studies were made using AFM (Thermomicroscopes Inc.; Autoprobe CP Research machine) in non-contact mode. For AFM studies silicon substrates were used with the same modification techniques as those described above for the QCM chips. The AFM tips used for imaging were silicon with an approximate radius of curvature of 20 nm. Biomolecular imaging was performed in non-contact mode. The AFM images were analyzed using image-processing software (IP 2.1) to calculate the RMS roughness value.

Results and Discussions

Protein A, which has a particularly high affinity for the $F_c$ fragment of IgG, was immobilized first on the chips to prevent the random immobilization of the antibodies, maximizing the ability of the chip immobilized antibodies to bind to antigens. H. Muramatsu, J. M. Dicks, E. Tamiya, I. Karube, "Piezoelectric crystal biosensor modified with protein A for determination of immunoglobulins", Analytical Chemistry 59 (1987) 2760-2763. F. Caruso, E. Rodda, D. N. Furlong, Oriental, "Aspects of Antibody Immobilization and Immunological Activity on Quartz Crystal Microbalance Electrodes", Journal of Colloid and Interface Science 178 (1996) 104-115.

Figure 11:
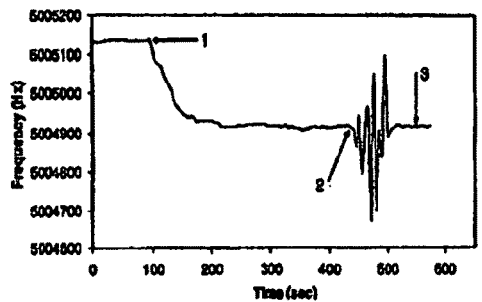
FIG. 11 is a graph showing the quartz crystal microbalance frequency response for Protein A immobilization without polystyrene.

FIG. 11 shows the QCM frequency response to Protein A immobilization without the polystyrene film. Point 1 refers to the point of addition of the Protein A containing solution to the chip. Point 2 indicates when the crystal was subjected to several wash-dry cycles and point 3 represents the frequency of crystal when Protein A was specifically bound on the surface. The frequency shift due to this direct binding was 220 Hz. From the Sauerbrey equation, this frequency shift corresponds to a 2.8 µg mass uptake.

Figure 12:
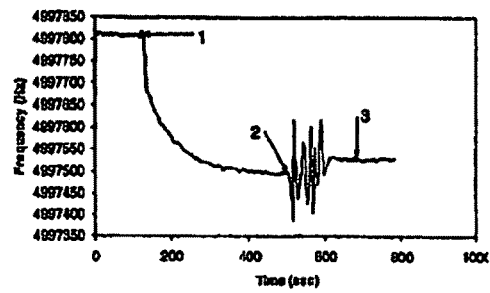
FIG. 12 is a graph showing the quartz crystal microbalance frequency response for IgG immobilization without polystyrene.

To determine if antibodies could bind to the Protein A that had been immobilized, antibody containing solutions were incubated with the chips. In FIG. 12, point 1 indicates the time at which the antibody containing solution was added to the crystal. The binding of the antibody to the immobilized Protein A caused a decrease in the resonant frequency and stabilization occurred after 15 minutes. Point 2 represents the time when the crystal was rinsed with 0.5M NaCl to remove any non-specifically adsorbed IgG and point 3 corresponds to the final resonant frequency after the NaCl rinsing. The frequency shift for IgG immobilization was found to be 282 Hz which corresponds to a calculated mass change of 3.61 µg.

Figure 13:
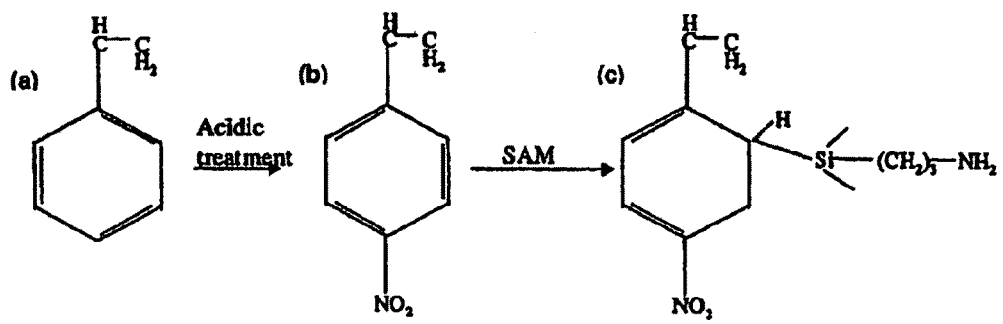
FIG. 13 shows the acidic treatment and APTES modification of polystyrene.

To determine if covering the chips with a thin polymer film could also increase the efficiency of Protein A binding and hence improvement in antibody immobilization, we coated the surface of several chips with ultra thin film of polystyrene. However, polystyrene films are hydrophobic in nature causing the biomolecules to denature and hence loose their activity. J. E. Butler, L. Ni, W. R. Brown, K. S. Joshi, J. Chang, B. Rosenberg, E. W. Voss, Jr., "The immunochemistry of sandwich elisas—VI. Greater than 90% of monoclonal and 75% of polyclonal antifluorescyl capture antibodies (Cabs) are denatured by passive adsorption", Molecular Immunology 30 (1993) 1165-1175. To avoid denaturation of the biomolecules, the polymer film functional groups such as amino, hydroxyl groups can be chemically added. This helps the biomolecules retain their activity as immobilization now takes place through the hydrophilic arms of the polymer film. J. Buijs, J. W. T. Lichtenbelt, W. Norde, J. Lyklema, "Adsorption of monoclonal IgGs and their F(ab')$_2$ fragments onto polymeric surfaces", Colloids and Surfaces B: Biointerfaces 5 (1995) 11-23. N. Zammatteo, C. Girardeaux, D. Delforge, J. J. Pireaux, J. Remacle, "Amination of Polystyrene Microwells: Application to the Covalent Grafting of DNA Probes for Hybridization Assays", Analytical Biochemistry 236, (1996) 85-94. To increase the hydrophilicity of the surface which would increase the ability to add the functional groups, the chips were subjected to an acidic treatment followed by aqueous silanization. J. Kaur, K. V. Singh, M. Raje, G. C. Varshney, C. R. Suri, "Strategies for direct attachment of hapten to a polystyrene support for applications in enzyme-linked immunosorbent assay (ELISA)", Analytica Chimica Acta 506 (2004) 133-135. FIG. 13 shows the schematic representation of the acidic treatment and the APTES modification of polystyrene. The acid treatment provides $NO_2$ groups and the APTES modification creates a polymer film with an amine group that can react with the glutaraldehyde used to covalently attach the biomolecules to the surface. This improvement in the hydrophilicity was confirmed by monitoring the water distribution on polystyrene and APTES modified polystyrene surfaces.

Figure 14:
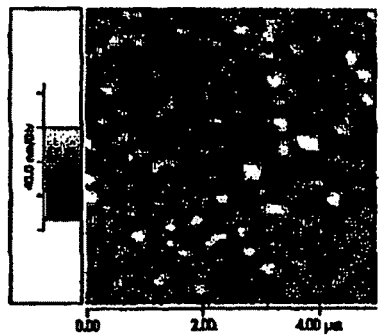
FIG. 14 is an AFM image of IgG immobilized on a polystyrene coated surface.

FIG. 14 shows the AFM image of IgG immobilized on polystyrene coated surface. It can be seen that there is a uniform coverage of the antibody molecules of approximately 10 nm in size on the substrate. The AFM imaging performed two hours after the biomolecules immobilization revealed that the molecules still retain their characteristic "heart shape" proving that they still are not denatured.

Figure 15:
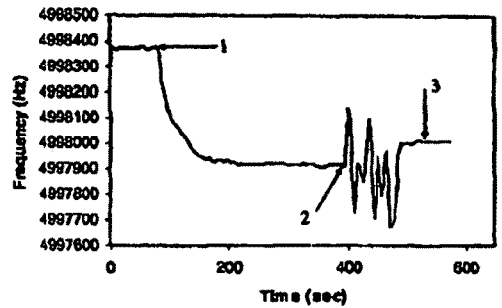
FIG. 15 is a graph showing the quartz crystal microbalance frequency response for Protein A immobilization on polystyrene.
Figure 16:
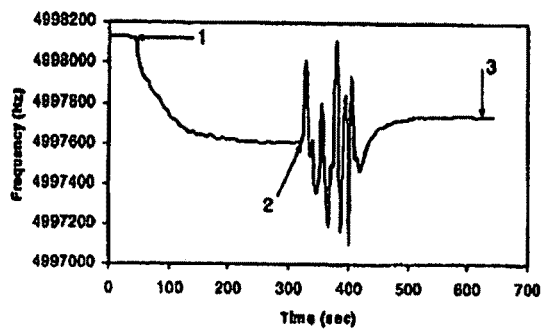
FIG. 16 is a graph showing the quartz crystal microbalance frequency response for IgG immobilization on polystyrene.

The biomolecule immobilization on polystyrene coated surfaces was then quantitatively studied with QCM and compared to the immobilization performed without polystyrene film. FIG. 15 shows the QCM response to Protein A immobilization. Point 1 indicates the time when Protein A was added and as can be seen, the signal became stable only after 20 minutes. Point 2 represents when several wash-dry cycles were performed and point 3 is the time at which the frequency stabilized once all non-specifically adsorbed molecules were rinsed away. The registered frequency shift was 364 Hz which corresponds to a mass change of 4.66 µg. This represented a 65% increase when compared to the QCM chips that were not coated with the polymer film. Similar results were obtained for the binding of IgG. The QCM response (FIG. 16) for IgG immobilization on the polystyrene surface showed a frequency shift of 391 Hz corresponding to a mass uptake of 5.01 µg. This represented a 40% increase when compared to chips that had not been modified with polystyrene.

We studied the height profile of the AFM images of the bare gold crystal and polystyrene coated crystal. The AFM studies revealed that the gold coated quartz crystals had a RMS surface roughness of 98.4 nm. An appreciable decrease in the surface roughness to 1.75 nm was observed when the crystal was coated with an ultra thin layer of polystyrene. Gold and polystyrene are both hydrophobic in nature. APTES modification of the gold surface although improves the hydrophilicity of the surface, it doesn't result in much decrease in the roughness of the surface. On the other hand, APTES modification of the polystyrene coated surface not only improves the hydrophilicity of the surface but there is a marked improvement in the surface roughness because of the polymer film. The improved biomolecular binding and hence the increased frequency shifts may be attributed to this improvement in the surface smoothness.

We speculate that with a gold surface roughness of 98.4 nm, the orientation of the protein A molecules is not uniform and hence there are chances that the active sites on one protein molecule would sterically hinder the active sites resulting in a nonuniform binding of biomolecules and hence loss of active sites. On the other hand, a polymer coated surface although decreases the available surface area, provides the biomolecules with a much more plane and uniform surface resulting in less steric hindrance. Hence more active sites for antibody immobilization are available resulting in improved binding and hence higher sensitivity.

CNT experiments were performed using 5 MHz AT-cut Quartz crystals coated with carbon nanotubes casted on the gold surface of the chip. Then the chip was baked at 50° C. for one hour. The presence of the CNT on the gold surface was confirmed by Raman spectroscopy.

The quantitative study of mass uptake of CNT network due to biomolecules immobilization was performed using QCM. In this part, the chemical interface is the CNT matrix on the gold surface coated on the QCM crystal. Measurements of CNT coated QCM crystals were performed by covering the chips with PBS before addition of the protein solutions.

Figure 17:
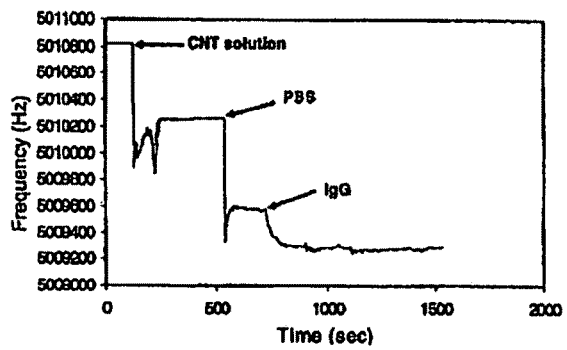
FIG. 17 is a graph showing the quartz crystal microbalance frequency response for various concentrations of IgG.

Similar experiments were performed with IgG and the frequency change was 248 Hz using a 2 µM concentration. FIG. 17 shows the QCM response for the IgG incubation. When the crystal was resonating at its natural frequency, the carbon nanotube solution was introduced on to the chip. After the chloroform evaporated, the frequency stabilized and the CNT formed a uniform matrix on the surface. Then PBS was introduced on to the chip and due to change in the viscosity a frequency shift was recorded. After the frequency stabilized, finally the IgG antibody was introduced and the frequency change of 248 Hz was recorded for a concentration of 2 µM. This frequency corresponds to mass of 3.17 µg. The frequency shift was found to be approximately 50 Hz for same concentration of IgG immobilized directly on the gold surface which suggests that there is a five fold increase in the number of biomolecules bound when CNT was used as chemical interface. Key research accomplishments of this preliminary data include:

Ultrathin polystyrene polymer films can be used to enhance the sensitivity and these films can be chemically treated to provide necessary terminal groups to tether biomolecules to the surface.

A 40% to 60% improvement in sensor sensitivity was demonstrated with aqueous silanization was achieved.

Novel nanostructure materials like carbon nanotubes have been integrated with existing technologies to push the detection limit of acoustic wave based sensors.

CNT based interfacial layer showed five fold improvement of the sensor response.

The present invention demonstrates a simple and efficient method for purification of carbon nanotubes for the fabrication of conductometric biosensor. Two schemes of biomolecular sensing using carbon nanotubes have been demonstrated. The conductance based sensors exhibited a decrease in the current level due to the noncovalent binding of the biomolecules on the sidewall of the CNTs. QCM experiments quantified the mass of the biomolecule bound on the CNT matrix.

The integrated microsystem of the present invention can also be used in the early detection of breast cancer by analyzing for breast epithelial mucin MUC-1, also known as carbohydrate antigen 15-3 or CA 15-3, peanut reactive urinary mucin or PUM, polymorphic epithelial mucin or PEM, epithelial membrane antigen or EMA, nonpenetrating glycoprotein or NPGP and episalin, in the serum of a subject. An antibody specific to MUC-1 is immobilized on the sensor surface and used to detect the presence of MUC-1 in the subject's serum.

What is claimed is:

1. An integrated microsystem for detecting biomolecules in liquid, comprising:
    a carbon nanotube sensor comprising a plurality of microelectrodes connected to a matrix of carbon nanotubes deposited on a substrate;
    a micropump;
    a microcontroller for controlling the micropump;
    a signal processor for analyzing the sensor signal;
    a microheater that surrounds the carbon nanotube sensor; and
    a microfluidic channel formed by a polydimethylsiloxane (PDMS) silicone elastomer cap containing a trench, wherein the cap is aligned with said carbon nanotube sensor.

2. The integrated microsystem of claim 1, wherein the carbon nanotube sensor includes a detector for detecting changes in electrical conductance or in resonant frequency in a carbon nanotube matrix and determining the quantity of mass uptake on biomolecule incubation.

3. The integrated microsystem of claim 2, wherein said detector operates to apply a constant voltage across the carbon nanotube matrix.

4. The integrated microsystem of claim 1, wherein said micropump is a flexural plate wave micropump.

5. The integrated microsystem of claim 2, wherein said sensor comprises a quartz crystal microbalance.

6. The integrated microsystem of claim 5, wherein said quartz crystal microbalance comprises carbon nanotubes deposited on gold-coated quartz crystals.

7. The integrated microsystem of claim 1, wherein said carbon nanotube sensor is a single wall carbon nanotube biological sensor.

8. The integrated microsystem of claim 5, wherein said quartz crystal microbalance comprises quartz crystals having polystyrene deposited thereon.

9. A method for detecting the presence of a biomolecule in a solution, comprising:
    providing an integrated microsystem, wherein the microsystem comprises a carbon nanotube sensor comprising a plurality of microelectrodes connected to a matrix of carbon nanotubes deposited on a substrate; a micropump; a microcontroller for controlling the micropump; a signal processor for analyzing the sensor signal; a microheater that surrounds the carbon nanotube sensor; and a microfluidic channel formed by a polydimethylsiloxane (PDMS) silicone elastomer cap containing a trench, wherein the cap is aligned with the carbon nanotube sensor; and detecting, using the integrated microsystem, the presence of the biomolecule in the solution by bringing the solution into contact with the carbon nanotube sensor; and determining the change in electrical conductance or resonant frequency of the carbon nanotube matrix.

10. The method of claim 9, wherein said micropump is a flexural plate wave micropump.

11. The method of claim 9, wherein the microcontroller controls the micropump.

* * * * *